United States Patent [19]

Lin et al.

[11] Patent Number: 4,828,672
[45] Date of Patent: May 9, 1989

[54] UNITARY SELF-GENERATING REFERENCE GAS SENSOR

[75] Inventors: Ching-Yu Lin, Monroeville, Pa.; Chikara Hirayama, Kaunakakai, Hi.

[73] Assignee: Westinghouse Electric Corp., Pittsburgh, Pa.

[21] Appl. No.: 175,434

[22] Filed: Mar. 30, 1988

[51] Int. Cl.$^4$ .............................................. G01N 27/46
[52] U.S. Cl. ..................................... 204/424; 204/427
[58] Field of Search ........................... 204/15, 421–429

[56] References Cited

U.S. PATENT DOCUMENTS

| | | | |
|---|---|---|---|
| 3,915,830 | 10/1975 | Isenberg | 204/426 |
| 4,284,486 | 8/1981 | Shinohara et al. | 204/424 |
| 4,295,939 | 10/1981 | Poirier et al. | 204/15 |
| 4,377,460 | 3/1983 | Hirayama et al. | 204/15 |
| 4,388,155 | 6/1983 | Chamberland et al. | 204/426 |
| 4,391,690 | 7/1983 | Lin et al. | 204/428 |
| 4,394,240 | 7/1983 | Pebler | 204/15 |
| 4,399,017 | 8/1983 | Inoue et al. | 204/425 |
| 4,427,525 | 1/1984 | Lin et al. | 204/427 |
| 4,622,105 | 11/1986 | Liu et al. | 204/424 |
| 4,715,944 | 12/1987 | Yanagida et al. | 204/426 |

*Primary Examiner*—T. Tung
*Attorney, Agent, or Firm*—Daniel P. Cillo

[57] ABSTRACT

A solid electrolyte gas sensor 10 is made, containing a body of solid electrolyte 14, in contact with a monitor electrode 12 exposed to a monitored gas environment 13 containing selected gas components to be measured, and in contact with a reference electrode 15 which is isolated from the monitored gas environment, where the solid electrolyte at the operating temperature of the gas sensor is effective to dissociate to provide the sole source of a self-generated gas, at the reference electrode 15, corresponding to the selected gas component to be measured.

13 Claims, 3 Drawing Sheets

UNITARY SELF-GENERATING REFERENCE GAS SENSOR

BACKGROUND OF THE INVENTION

1. Field of the Invention

This invention relates to unitary, self-generating reference gas sensors, useful to detect $SO_2$, $CO_2$ and $NO_2$ gases.

2. Description of the Prior Art

The requirements for monitoring and controlling stack gas pollutants have resulted in the development of solid electrolyte gas sensors having electrolyte compostions uniquely responsive to gases such as $SO_2$, $CO_2$ and $NO_2$. These sensors are electrochemical concentration cells which sense the equilibrium of a gas species of interest and generate an EMF signal corresponding to the difference in partial pressure of the gas species across the solid electrolyte sensor. Typically, the solid state sensor includes an ion conductive solid electrolyte with electrodes disposed on its opposite surfaces. The stack gas, or monitored gas stream, contacts a sensing electrode, while the opposite electrode serves as a reference electrode which is contacted with a reference gas stream. Conventional solid electrolyte compositions require operating temperatures of between 200° C. and 900° C. to exhibit the desired ion conductivity to generate a suitable EMF signal.

In the past, a major problem with these devices was isolation of the monitored gas from the reference gas, to prevent unpredictable drift in the measurement signal. Hirayama et al., in U.S. Pat. No. 4,377,460, solved this sealing problem by using a closed end, gas impermeable, mullite ($3Al_2O_3 \cdot 2SiO_2$) tube, which acts as an alkali ion conductive membrane at high temperatures. The mullite tube, like most ceramics, incorporates some alkali oxide impurities, such as $K_2O$, making it a $K^+$ ionic conductor at high temperatures. This tube was used to separate the two gas streams and provide two identical alkali ion conductive half cells secured to opposite sides of the mullite.

The two, alkali ion conductive solid electrolyte disc used in each half cell of the Hirayama et al. design, to monitor $SO_2$, $CO_2$ or $NO_2$, were made of $K_2SO_4$, $Na_2CO_3$, or $NaNO_3$ respectively. A platinum electrode was attached to one side of each half cell electrode. In the case of a $SO_2+O_2$ reference gas stream, this provided the cell assembly:

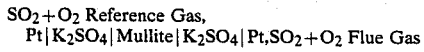

$SO_2+O_2$ Reference Gas,
Pt|$K_2SO_4$|Mullite|$K_2SO_4$|Pt,$SO_2+O_2$ Flue Gas

Lin et al., in U.S. Pat. No. 4,427,525, taught a somewhat similar system using calcia stabilized zirconia as the solid electrolyte. These sensor designs, however, are complicated to make and operate. Also, this use of a $SO_2+O_2$ reference gas stream is inconvenient and expensive, since a constant supply of certified tank gas is required.

Several instances of simplified, unitary gas sensors have been disclosed in the art. Isenberg, in U.S. Pat. No. 3,915,830, relating to $O_2$ sensors, taught hermetically encapsulating a metal/metal oxide reference medium, such as nickel/nickel oxide, exhibiting a stable oxygen activity, within a small, stabilized zirconia solid electrolyte disc. A metal electrode is attached to the outside of the solid electrolyte and is in electronic communication with the encapsulated reference medium. Sealing other reference media, such as oxygen gas or air within the solid electrolyte is also mentioned. Inoue et al., in U.S. Pat. No. 4,399,017, taught encapsulation of an electrode within a microporous, stabilized zirconia solid electrolyte. A second electrode is attached to the outside of the solid electrolyte, and the whole covered with porous ceramic. Upon application of a D.C. current, migration of oxygen ions, and diffusion of oxygen gas through the microporous solid electrolyte, can establish a reference partial pressure of oxygen at the interface between the microporous solid electrolyte and the encapsulated electrode, to enable measurement of oxygen gas content in flue gas.

Pebler, in U.S. Pat. No. 4,394,240, taught triangular, combination electrochemical cells, which form an internal cavity which contains a common internal gas forming reference. In the triangular configuration, two sides are made of stabilized zirconia, oxygen ion conductive solid electrolyte, and the third side can be made of $K_2SO_4$ when $SO_3$ or $SO_2$ gases are to be measured. Reference electrodes are disposed on the inside electrolyte walls of the triangular configuration and sensing electrode are disposed on the outside electrolyte walls. The measuring concept utilizes heating a central, enclosed, $MgSO_4$, $MnSO_4$ or $Ag_2SO_4$ reference material, which provides $SO_3$ on decomposition. This reference material must be kept sealed from $K_2SO_4$ electrolyte, because of the possible reaction of these two components at high temperatures.

None of these designs provide a simple, inexpensive construction that would be effective to measure $SO_2$, $CO_2$ or $NO_2$ content of flue gases. It is an object of this invention to provide such a construction.

SUMMARY OF THE INVENTION

Accordingly, the invention resides in a solid electrolyte gas sensor apparatus for measuring selected gas components of a monitored gas environment, by generating an electrical signal on the basis of a difference in the partial pressure between the selected component gas of the monitored gas environment, at a first monitor electrode in contact with the monitored gas environment and solid electrolyte, and the corresponding gas component of a reference gas environment, at a second reference electrode in contact with the reference gas environment and solid electrolyte; characterized in that the electrolyte itself, upon the application of heat, is effective to disassociate to provide the sole source of a constant partial pressure of self generated gas, at the reference electrode, corresponding to the selected gas component to be measured. This provides a unitary gas sensor apparatus, where solid electrolyte is effective to prevent monitored gas contact with the second reference electrode.

Also included are measuring circuit means connected to said first and second electrodes of the cell, which is effective to generate an electrical signal measurement of the selected gas component in the monitored gas environment. When the selected gas component to be monitored is $SO_2$, the solid electrolyte will be selected from $K_2SO_4$ and $Na_2SO_4$. When the selected gas component to be monitored is $CO_2$ or the like gases, the solid electrolyte will be selected from $K_2CO_3$ and $Na_2CO_3$. When the selected gas component to be monitored is $NO_2$ or the like gases, the solid electrolyte will be selected from $KNO_3$ and $NaNO_3$.

Thus, there is no need to supply any reference gas in the reference system. Additionally, this single-cell sensor can be miniaturized and its manufacture and operation can provide substantial cost savings. The preferred electrodes are platinum, and the portion of the unitary sensor not to be contacted by the monitored gas environment can be enclosed in a gas impermeable, high temperature stable, ceramic, sealing material. This sensor is effective within the temperature range of 200° C. to 900° C.

BRIEF DESCRIPTION OF THE DRAWING

In order that the invention can be more clearly understood, convenient embodiments thereof will now be described, by way of example, with reference to the accompanying drawings in which.

DESCRIPTION OF THE PREFERRED EMBODIMENTS

Figure 1:
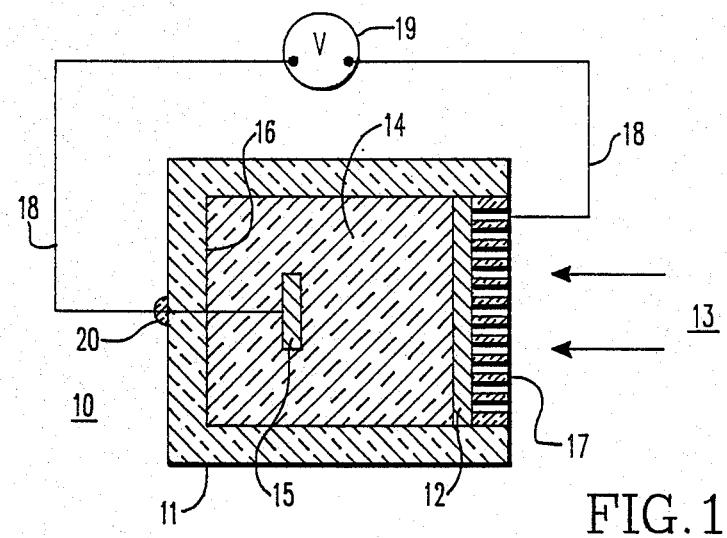
FIG. 1 is a cross-sectional view of one embodiment of a unitary, single cell, self-generating reference gas sensor of this invention.

Referring now to FIG. 1, solid electrolyte, unitary, gas sensor electrochemical cell 10 is shown. This single sensor cell is contained within a non-porous, high temperature stable, gas impermeable vessel 11, usually a dense ceramic cylindrical cup or bored out tube made of, for example, alumina, mullite ($Al_2O_3 \cdot 2SiO_2$), magnesia, zirconia, and the like, preferably of at least 90% purity. These materials would be isostatically pressed at high temperatures, to provide a sintered, high density (at least 90% dense) cup or tube. A first, metal, monitor electrode 12, contacts both the monitored gas environment 13, containing the gas component to be measured, and the single body of solid oxide electrolyte 14 contained in the sensor cell.

A second, metal, reference electrode 15, may be completely encapsulated, surrounded, and contacted by electrolyte 14, or may be disposed against an inner wall of the containment vessel, as at point 16, and contacted by electrolyte. The solid electrolyte 14, in either case, will preferably be at least 95% dense, and will be of at least 95% purity. The solid electrolyte will be made from sintered, submicron particles, preferably in a range from approximately 0.1 micron to 0.9 micron, and will be effective to prevent monitored gas 13 contact with the reference electrode 15. The preferred material for electrodes 12 and 15 as well as electrical leads 18 is platinum.

A porous, gas dispersing ceramic spacer 17 may be used to assure uniform contact of the monitored gas environment 13 with the monitor electrode 12. Measuring circuit means, comprising electrical lead wires 18 connected to the electrodes 12 and 15, as well as voltmeter 19 are shown. This circuit responds to electrical signals generated, and provides an indication of both the partial pressure of selected gas component in the monitored gas environment and the partial pressure of the corresponding similar gas generated by decomposition of the electrolyte. A high temperature stable ceramic oxide sealant 20, such as, for example a mixture of 49 wt. % CaO, 49 wt. % $Al_2O_3$ and 2 wt. % $SiO_2$, having a melting point of approximately 1430° C., is used to ensure isolation of monitor electrode 12. The main body of this gas sensor cell can be inserted or assembled into a probe structure, having a heating element and temperature control, to provide a gas sensing apparatus.

The EMF (electromotive force) signal generated by the solid electrolyte gas sensor cell, is developed in accordance with the well known Nerst equation, where the variables include the cell temperature, and the variation of partial pressure of the gas component of interest in the monitored gas environment at the monitor electrode 12, and the partial pressure of the same reference gas at the reference electrode 15. In this invention, the solid electrolyte itself, upon the application of heat, is effective to dissociate to provide the sole source of reference gas.

In the case where the monitored gas environment contains $SO_2$ and $O_2$, and where the solid electrolyte is $K_2SO_4$, upon operation of the gas sensor cell at from 600° C. to 900° C., the solid electrolyte will be in equilibrium dissociation to provide a $SO_2+O_2$ reference gas, according to the chemical reaction:

$$K_2SO_4 \rightleftharpoons 2K^+ + SO_2 + O_2.$$

In this case, the EMF would be calculated from the equation:

$$EMF = \frac{RT}{2F} \ln \frac{P_{SO_2} \cdot P_{O_2}}{P'_{SO_2} \cdot P'_{O_2}},$$

where
 R = the universal gas constant,
 T = temperature °K.,
 F = Faraday Constant (23,061 cal./volt),
 P = partial pressure of reference $SO_2$ and $O_2$, and
 P' = partial pressure of monitored $SO_2$ and $O_2$,
 where R, T, F, and P are known.

From this equation, a direct measurement of $SO_2$ plus $O_2$ component gases in the monitored gas environment can be made by the measurement of the EMF of the censor cell. This design would measure $SO_2+O_2$, $CO_2+O_2$, or $NO_2+O_2$, so that a separate $O_2$ sensor would be installed, and the $O_2$ concentration, in terms of voltage output, would be compensated for electronically.

When the selected gas component to be monitored is $SO_2$, the solid electrolyte will be selected from $K_2SO_4$ and $Na_2SO_4$. At 600° C. to 900° C. sensor operation, solid $K_2SO_4$ will be in equilibrium dissociation with $2K^+ + SO_2 + O_2$. At 600° C. to 880° C. sensor operation, solid $Na_2SO_4$ will be in equilibrium dissociation with $2Na^+ + SO_2 + O_2$. When the selected gas component to be monitored is $CO_2$, the solid electrolyte will be selected from $K_2CO_3$ and $Na_2CO_3$. At 600° C. to 800° C. sensor operation solid $K_2CO_3$ will be in equilibrium dissociation with $2K^+ + CO_2 + \frac{1}{2}O_2$ and solid $Na_2CO_3$ will be in equilibrium dissociation with $2Na^+ + CO_2 + \frac{1}{2}O_2$. When the selected gas component to be monitored is $NO_2$ or NO, the solid electrolyte will be selected from $KNO_3$ and $NaNO_3$. At 200° C. to 300° C. sensor operation, solid $KNO_3$ will be in equilibrium dissociation with $K^+ + NO_2 + \frac{1}{2}O_2$ and solid $NaNO_3$ will be in equilibrium dissociation with $Na^+ + NO_2 + \frac{1}{2}O_2$. This last sensor can be operated only at low or cooled flue gas temperatures.

In all instances, at the operating temperature of the sensor cell, the solid electrolyte itself is effective to prevent monitored gas from reaching the reference electrode, provides alkali ion conductivity, and provides the sole source $SO_2$, $CO_2$ or $NO_2$ reference gas, depending on the solid electrolyte used. The amount of $SO_2$, $CO_2$ or $NO_2$ generated by equilibrium dissociation of the solid electrolyte will be on the order of 0.5 ppm (parts per million) to 100 ppm, whereas the amount of $SO_2$, $CO_2$ or $NO_2$ in the monitored gas environment may be from 500 ppm to 2500 ppm, in most cases. There is no separate, exterior reference gas stream associated with this sensor apparatus. The only useful cations are $K^+$ and $Na^+$, as they provide the best combination of low electrolyte resistance and highest decomposition temperature for the anions used.

Ideally, the partial pressure of $SO_2$ and $O_2$ or other dissociation gas species at the reference electrode 15, would be equivalent to the true dissociation pressure of $K_2SO_4$, or the other useful solid electrolytes described hereinbefore, at a controlled temperature, if the reference electrode is perfectly sealed in the solid electrolyte without formation of any minute voids. Presence of minute voids in the solid electrolyte could trap a variety of gas species during the electrolyte fabrication process, and could also accumulate $SO_2$ and $O_2$ gases from the dissociation reaction of the solid electrolyte during sensor cell operation. An essentially void free solid electrolyte is strived for in this invention. The preferred solid electrolyte in this invention will be substantially free of minute voids. It will preferably be at least from 95% to 98% dense.

Since any voids present in the solid electrolyte would be minute under presently used powder sintering techniques, and they would be either hermetically sealed or confined in a small space, these trapped gas species would tend to be in equilibrium with the solid electrolyte at a controlled temperature. Therefore, a stable and constant partial pressure of $SO_2+O_2$, or $CO_2+O_2$, or $NO_2+O_2$ is expected to be maintained at the reference electrode, which would result in a stable and reproducible EMF measurement. What is essential is to establish a constant partial pressure of $SO_2+O_2$, or $CO_2+O_2$, or $NO_2+O_2$ at the reference electrode during sensor cell operation.

Figure 2:
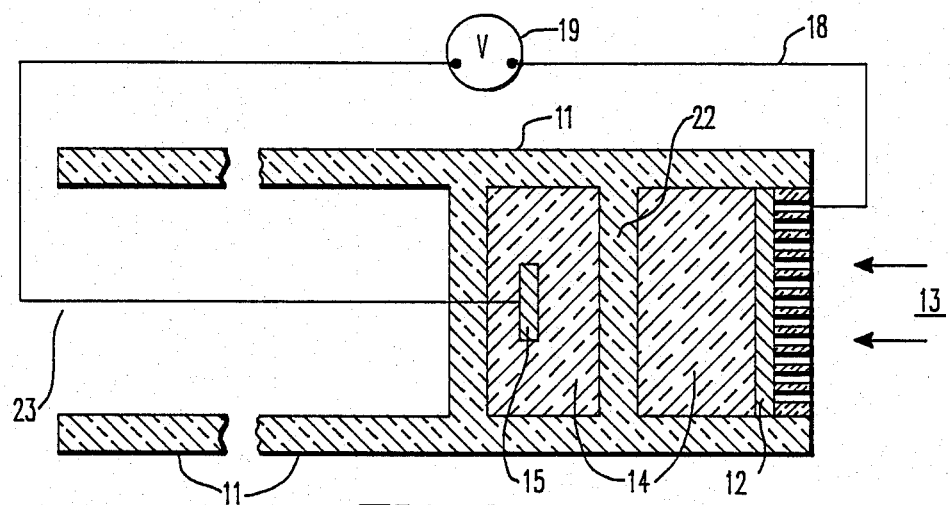
FIG. 2 is a cross-sectional view of another embodiment of the sensor of this invention, where each electrode physically contacts electrolyte but the electrolyte is split into two sections separated by a potassium or sodium ion conductive material.

Another embodiment of this invention is shown in FIG. 2, where each electrode 12 and 15 physically contact electrolyte 14, but where the electrolyte is split into two portions separated by an extension 22 of the gas impermeable vessel 11. In this instance, the gas impermeable vessel 11 and its extension 22 will be made of a potassium or sodium ion conductive material, such as a mullite ($3Al_2O_3 \cdot 2SiO_2$) material which contains alkali oxide impurities, such as $Na_2O$, $K_2O$ and the like, making it a $K^+$ and/or $Na^+$ conductive membrane. The self-generating reference gas function of solid electrolyte in contact with the reference electrode 15 remains the same as in the device of FIG. 1. This embodiment can be in the form of a long tube, end 23 of which can be far removed from the monitored gas environment 13. This embodiment could be substituted for the long tubular inner reference cell in sensors described in U.S. Pat. Nos. 4,377,460 and 4,427,525.

The gas sensor cell can be made by providing a high density cylindrical cup of high purity gas impermeable alumina. A small hole can be drilled at the closed end, a platinum reference electrode disc positioned inside the cup near the closed end, and a platinum lead wire inserted through the hole and soldered to the electrode. High temperature ceramic sealent can be used over the drilled hole on the outside of the alumina cup. Then, a fine powder of potassium or sodium sulfate, potassium or sodium carbonate or potassium or sodium nitrate can be packed into the alumina cup and around the reference electrode. This alkali salt would then be press sintered at a temperature about 100° C. below its melting point. Melting points are 1072° C. for potassium sulfate, 891° C. for potassium carbonate, and 337° C. for potassium nitrate. This will provide an essentially void free, gas impermeable, solid electrolyte, preferably with no cracking upon cooling.

A platinum monitor electrode can then be placed on top of the solid electrolyte across the opened end top of the enclosing cup, and platinum lead wire soldered in place. Finally, a porous, ceramic gas dispersing grid can be sealed on top of the monitor electrode. The leads can then be connected to gas monitoring circuitry, usually including a voltmeter, and the gas sensor cell placed in a monitoring gas environment, usually in an encasing probe means with a heater and heater controls, and operated at an operating temperature effective to cause equilibrium dissociation of the solid electrolyte. The sensor must be operated at a temperature substantially below the melting point of the solid electrolyte.

The invention will now be illustrated by the following EXAMPLE.

EXAMPLE

A single cell, self-generating reference gas sensor, similar to that shown in FIG. 1, was made. A high purity (99+%) alumina, closed end tube, approximately 1 cm long, 1 cm in outside diameter, and 0.2 cm thick, isostatically pressed to 98% density, was drilled at the middle of the closed end to provide a small hole about 1 mm. in diameter. Platinum wire was inserted through the hole, wound as a support, and soldered to a platinum electrode screen having a diameter of approximately 0.8 cm, held in place within the tube, Powdered, 99% pure $K_2SO_4$, having a submicron particle size, was poured into the bottom of the tube, around the electrode, and on top of the electrode to the top of the tube and tamped in place.

The $K_2SO_4$ filled tube was then hot pressed with a plunger at approximately 980° C. This caused the $K_2SO_4$ particles to come into very intimate contact, and to heatsinter together, to form an essentially void free, 98% dense, solid electrolyte structure. An exterior, platinum monitor electrode screen was then pressed and bonded to the top of the solid electrolyte. Platinum wire was then attached to the monitor electrode. Both wire leads from the monitor electrode and encapsulated interior sensing electrode were connected to a Keithley digital voltmeter. The whole sensor was assembled into a probe structure having a heating element and temperature control to provide a gas sensor apparatus.

As a control apparatus, a standard $SO_2+O_2$ sensor, as substantially described in U.S. Pat. No. 4,377,460, utilizing two $K_2SO_4$ solid electrolyte cells separated by a mullite tube, and being fed a reference gas stream of 100 ppm. of $SO_2$ in air from certified gas tanks was used. Both sensor apparatus were placed in a gas environment containing varying amounts of SO₂, at a controlled temperature, and EMF values were measured. It appeared that the partial pressure of $SO_2$ and $O_2$ at the platinum reference electrode of the self-generating reference gas sensor was higher than that of the true dissociative pressure of $K_2SO_4$. Both apparatus were calibrated as follows in TABLE 1, where the reference electrode was the positive electrode:

TABLE 1

|  | Self-Generating SO₂ Reference Gas Sensor | | Standard SO₂ Gas Sensor | |
| --- | --- | --- | --- | --- |
|  | Day 1 | Day 28 | Day 1 | Day 28 |
| Reference Gas Stream | NONE | | SO₂ in air | |
| T °C. | 852 | 854 | 820 | 813 |
| Monitored Gas Stream Composition: | | | | |
| 100 ppm SO₂ in air | −122EMF | −121EMF | +13EMF | +12EMF |
| 1000 ppm SO₂ in air | −233EMF | −232EMF | −118EMF | −109EMF |
| 5000 ppm SO₂ in air | −318EMF | −318EMF | −199EMF | −197EMF |
| 1.1% SO₂ in air | −358EMF | −356EMF | −237EMF | −236EMF |

Figure 3:
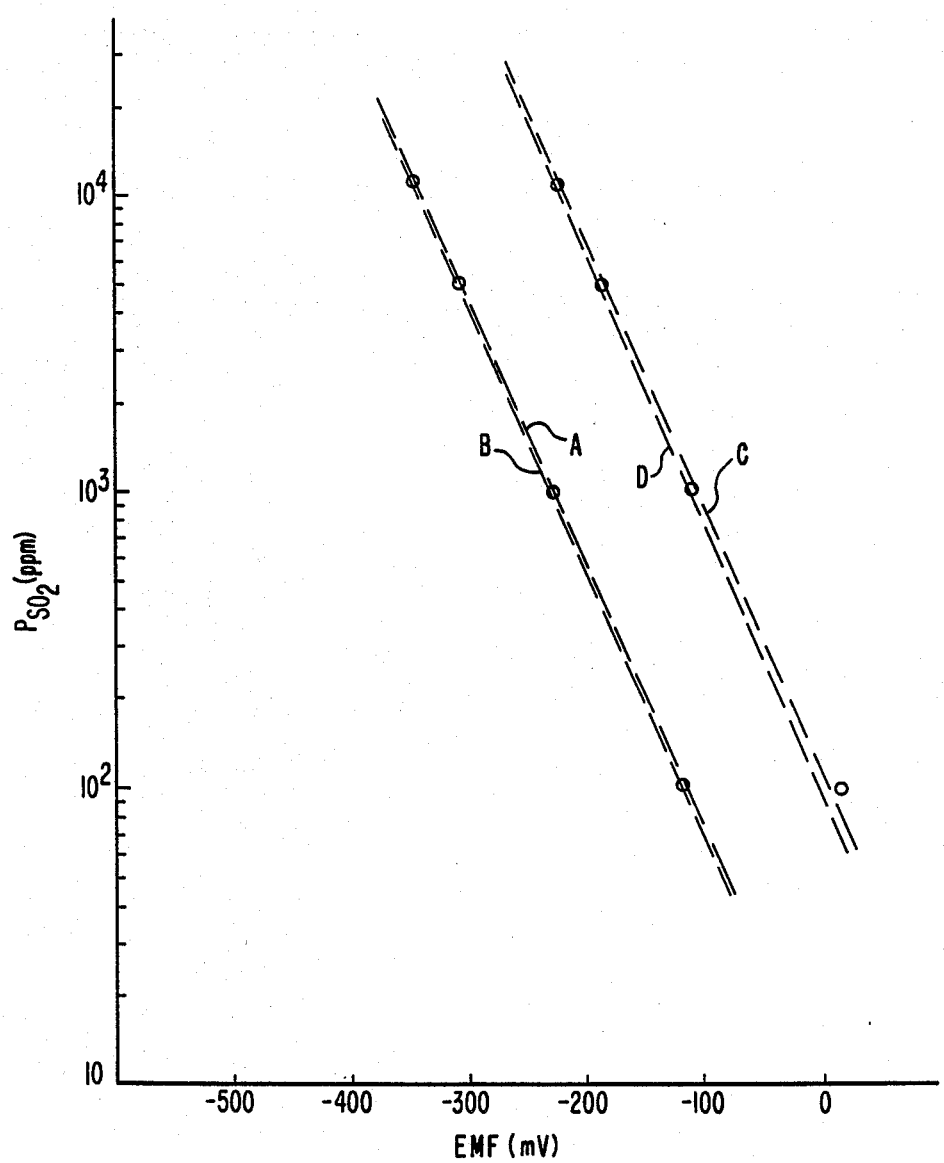
FIG. 3 shows calibration curves in $SO_2+$ air, of EMF vs. ppm $SO_2$, for the self-generating reference gas sensor of the invention, A and B, and a standard $SO_2$ gas sensor, C and D, both at controlled temperatures.

The slopes of the calibrations are shown in FIG. 3, EMF in mV vs PSO₂ in ppm in air, where slopes A and B are of the self-generating reference gas sensor of this invention at day 1 and day 28, respectively. Slopes C and D are of the standard, control, SO₂ gas sensor at day 1 and day 28, respectively. As can be seen, the slopes are almost exactly the same, with only minor drifting over the 28 day period. For about 8 months of life testing in the laboratory, both sensors behaved similarly. The slopes of the calibration curves of both sensors approximate the theoretically predicted curve.

Figure 4:
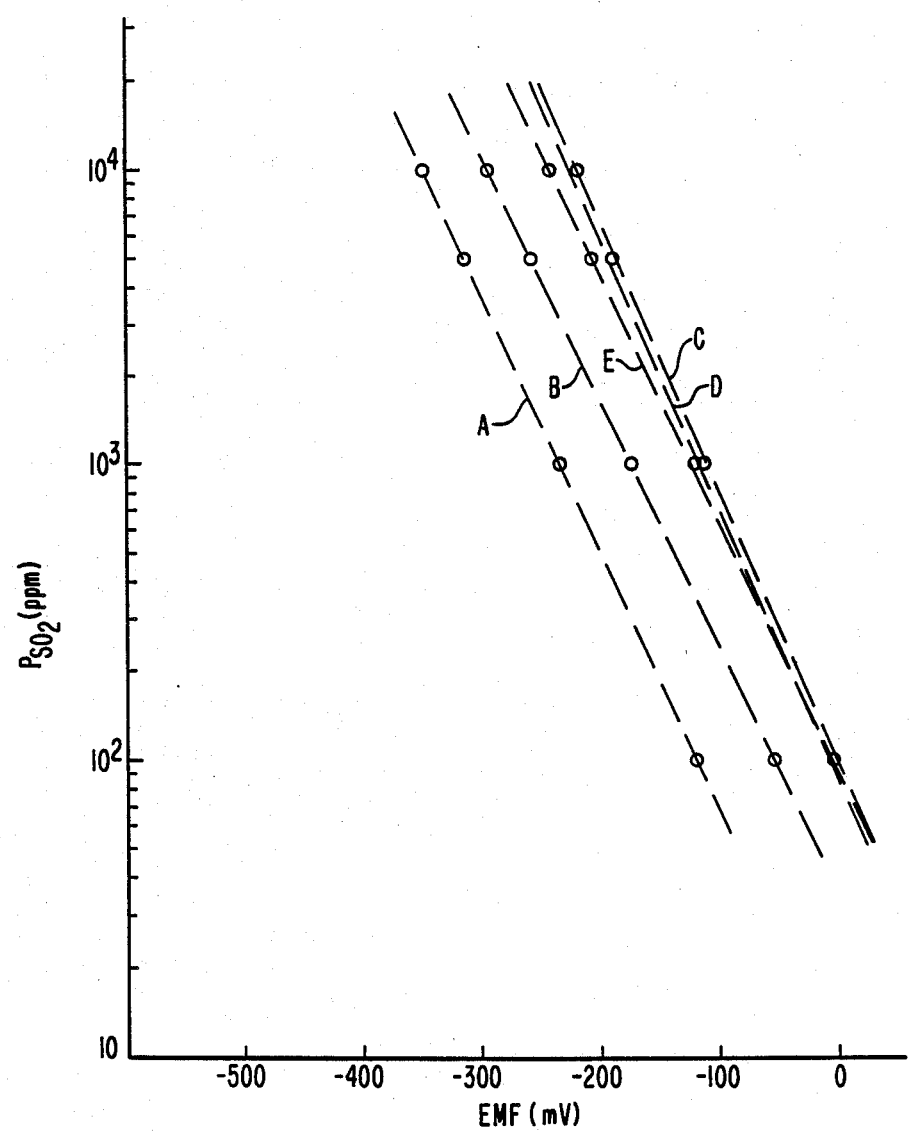
FIG. 4 shows calibration curves in $SO_2+$ air, of EMF vs. ppm $SO_2$, for the self-generating reference gas sensor of this invention, A and B, and a standard $SO_2$ gas sensor, C, D and E, both at widely varied temperatures.

The same two sensors were used to study the effect of temperature on the behavior of both sensors during the life testing period. FIG. 4, a graph of EMF in mV vs PSO₂ in ppm in air, shows the effect of cell temperature on the SO₂ calibration curves of both sensors. A large temperature effect was observed for the calibration curves of sensor using the self-generating reference gas, while the effect of the temperature on the calibration curves on the standard sensor, using 100 ppm SO₂ in air as a reference gas, was relatively small.

Curves A and B in FIG. 4 show the calibration curves for the self-generating reference gas sensor at 854° C. and 901° C., respectively. Curves C, D, and E show the calibration curves for the standard, control, SO₂ gas sensor at 765° C., 820° C. and 867° C., respectively. The large temperature effect on the cell EMF when using the self reference electrode is due to the large effect of temperature on the equilibrium of the existing gases and the solid $K_2SO_4$ at the reference electrode, which results in a large partial pressure of SO₂ and O₂ change at the electrode when the cell temperature varied. However, when the cell temperature is controlled at a fairly constant level, both sensors behaved reliably. This effect should have no effect on performance or reliability as long as the temperature is kept relatively constant.

We claim:

1. A solid electrolyte gas sensor for measuring a selected component gas of a monitored gas environment, by generating an electrical signal on the basis of a difference in the partial pressure between the selected component gas of the monitored gas environment at a monitor electrode in contact with the monitored gas environment and a solid electrolyte, and a corresponding component gas of a reference gas environment at a reference electrode in contact with the reference gas environment and the solid electrolyte; the improvement characterized in that the reference electrode is platinum and is isolated from the monitored gas environment, said solid electrolyte has a single component composition and is adapted upon heating to dissociate and provide the sole source of reference gas at the reference electrode, corresponding to the selected component to be measured, to provide a unitary gas sensor.

2. The solid electrolyte gas sensor of claim 1, wherein the reference electrode is embedded in the electrolyte, said electrolyte being effective to prevent contact of the monitored gas environment with the reference electrode.

3. The solid electroltye gas sensor of claim 1, wherein the electrodes are metal electrodes that are attached to a circuit means which is effective to generate an electrical signal measurement of the selected component gas in the monitored gas environment.

4. The solid electrolyte gas sensor of claim 1, wherein the solid electrolyte is selected from one of the group consisting of $K_2SO_4$, $Na_2SO_4$, $K_2CO_3$, $Na_2CO_3$, $KNO_3$ and $NaNO_3$.

5. The solid electrolyte gas sensor of claim 1, wherein the portion of the sensor not to be contacted by the monitored gas environment is enclosed in a gas impermeable, high temperature stable, ceramic sealing material.

6. The solid electrolyte gas sensor of claim 1, wherein a stable and constant partial pressure of the reference gas is maintained at the reference electrode.

7. The solid electrolyte gas sensor of claim 1, wherein the solid electrolyte is selected from one of the group consisting of $K_2SO_4$ and $Na_2SO_4$, and the selected gas component present in the monitored gas environment is $SO_2$.

8. The solid electrolyte gas sensor of claim 1, wherein both electrodes physically contact the same body of electrolyte.

9. The solid electrolyte gas sensor of claim 1 wherein the electrolyte is split into two portions separated, by a potassium or sodium ion conductive material, with said electrodes being disposed on opposite sides of the ion conductive material.

10. A solid electrolyte gas sensor comprising a body of solid electrolyte in contact with a metal monitor electrode exposed to a monitored gas environment containing a selected component gas to be measured, and in contact with a metal reference electrode which is isolated from the monitored gas environment, wherein the reference electrode is platinum, and wherein the solid electrolyte has a single component composition and is adapted upon heating to dissociate and provide the sole source of reference gas at the reference electrode, corresponding to the selected component gas to be measured.

11. The solid electrolyte gas sensor claim 10, wherein the solid electrolyte is selected from one of the group consisting of $K_2SO_4$, $Na_2SO_4$, $K_2CO_3$, $Na_2CO_3$, $KNO_3$ and $NaNO_3$.

12. The solid electrolyte gas sensor of claim 10, wherein the portion of the sensor not to be contacted by the monitored gas environment is enclosed in a gas impermeable, high temperature stable, ceramic sealing material.

13. The solid electrolyte gas sensor of claim 10, wherein the solid electrolyte is selected from one of the group consisting of $K_2SO_4$ and $Na_2SO_4$, and the selected gas component present in the monitored gas environment is $SO_2$.

* * * * *